United States Patent
Winde et al.

(10) Patent No.: US 9,562,116 B2
(45) Date of Patent: *Feb. 7, 2017

(54) METHOD FOR PREPARATION OF RUTHENIUM-BASED METATHESIS CATALYSTS WITH CHELATING ALKYLIDENE LIGANDS

(71) Applicants: UMICORE AG & CO. KG, Hanau-Wolfgang (DE); GRAZ UNIVERSITY OF TECHNOLOGY, Graz (AT)

(72) Inventors: Roland Winde, Frankfurt (DE); Angelino Doppiu, Seligenstadt (DE); Eileen Woerner, Maintal (DE); Andreas Rivas-Nass, Schriesheim (DE); Ralf Karch, Kleinostheim (DE); Christian Slugovc, Graz (AT); Christina Schinagl, Kalsdorf (AT)

(73) Assignees: UMICORE AG & CO. KG, Hanau-Wolfgang (DE); GRAZ UNIVERSITY OF TECHNOLOGY, Graz (AT)

( * ) Notice: Subject to any disclaimer, the term of this patent is extended or adjusted under 35 U.S.C. 154(b) by 27 days.

This patent is subject to a terminal disclaimer.

(21) Appl. No.: 14/472,088

(22) Filed: Aug. 28, 2014

(65) Prior Publication Data
US 2014/0371462 A1   Dec. 18, 2014

Related U.S. Application Data

(63) Continuation of application No. 13/318,989, filed as application No. PCT/EP2010/002720 on May 4, 2010, now Pat. No. 8,846,938.

(30) Foreign Application Priority Data

May 7, 2009   (EP) .................................. 09006204

(51) Int. Cl.
| C07F 15/00 | (2006.01) |
| B01J 31/12 | (2006.01) |
| C08F 4/80 | (2006.01) |
| B01J 31/22 | (2006.01) |

(52) U.S. Cl.
CPC .............. C08F 4/80 (2013.01); B01J 31/2265 (2013.01); B01J 31/2278 (2013.01); C07F 15/0046 (2013.01); B01J 2231/543 (2013.01); B01J 2531/821 (2013.01)

(58) Field of Classification Search
USPC ......................... 548/103; 502/155
See application file for complete search history.

(56) References Cited

U.S. PATENT DOCUMENTS

| 6,921,735 B2 | 7/2005 | Hoveyda et al. |
| 7,205,424 B2 | 4/2007 | Nolan |
| 8,288,558 B2 * | 10/2012 | Arlt ........................ B01J 31/182 548/103 |
| 8,536,344 B2 * | 9/2013 | Arlt ........................ B01J 31/182 548/103 |
| 8,846,938 B2 * | 9/2014 | Winde ................ C07F 15/0046 502/155 |
| 2005/0261451 A1 | 11/2005 | Ung et al. |
| 2005/0272598 A1 | 12/2005 | Hoveyda et al. |
| 2010/0087644 A1 | 4/2010 | Mauduit et al. |
| 2010/0113795 A1 | 5/2010 | Arlt et al. |
| 2010/0174068 A1 | 7/2010 | Grela et al. |
| 2010/0292486 A1 | 11/2010 | Hoveyda et al. |

FOREIGN PATENT DOCUMENTS

| CA | 2663542 | 3/2008 |
| JP | 2007/501199 | 1/2007 |
| JP | 2007/530706 | 11/2007 |
| WO | 02/14376 | 2/2002 |
| WO | 2004/035596 | 4/2004 |
| WO | 2007/140954 | 10/2004 |
| WO | 2005/016944 | 2/2005 |
| WO | 2007/140954 | 12/2007 |
| WO | 2008/034552 | 3/2008 |
| WO | 2008/065187 | 6/2008 |

OTHER PUBLICATIONS

International Search Report for PCT/EP2010/002720 mailed Sep. 23, 2010 (in English).
S.B. Garber, et al,: "*Efficient and Recyclable Monomeric and Dendritic Ru-Based Metathesis Catalysts*" J. Amer. Chem. Soc. 2000, 122, 8168-8179.
S. Blechert et al.: "*Highly Selective Metathesis with Acrylonitrile Using a Phosphine Free Ru-Complex*" Synlett 2001, No. 3, 430-432.
A. Hejl, et al.: "*Latent Olefin Metathesis Catalysts Featuring Chelating Alkylidenes*" Organometallics 2006, 25, 6149-6154.
T. Ung, et al.: "*Latent Ruthenium Olefin Metathesis Catalysts That Contain an N-Heterocyclic Carbene Ligand*" Organometallics 2004, 2.3, 5399-5401.
M. Barbasievicz, et al.: "*Structure and Activity Peculiarities of Ruthenium Quinoline and Quinoxaline Complexes*" Novel Metathesis Catalysts, Organometallics 2006, 25(15), 3599-3604.

(Continued)

*Primary Examiner* — Charanjit Aulakh
(74) *Attorney, Agent, or Firm* — Smith, Gambrell & Russell, LLP

(57) ABSTRACT

The invention relates to a method for preparation of ruthenium-based carbene catalysts with a chelating alkylidene ligand ("Hoveyda-type catalysts") by reacting a penta coordinated ruthenium (II)-alkylidene complex of the type (L)(Py)X1X2Ru(alkylidene) with a suitable olefin derivative in a cross metathesis reaction. The method delivers high yields and is conducted preferably in aromatic hydrocarbon solvents. The use of phosphine-containing Ru carbene complexes as starting materials can be avoided. Catalyst products with high purity, particularly with low Cu content, can be obtained.

16 Claims, No Drawings

(56) References Cited

OTHER PUBLICATIONS

D. Burtscher, et al.: "*Controlled Living Ring-Opening Metathesis Polymerization with a Ruthenium Indenylidene Initiator*" J. of Polymer Science: Part A: Polymer Chemistry 2008, vol. 46, 4630-4635.
C. Slugove, et al.: "*Second Generation Ruthenium Carbene Complexes with a cis-Dichloro Arrangement*" Organometallics 2004, 23, 3622-3626.
Bernd Schmidt, et al.: "*Synthesis of dihydrofurans and dihydropyrans with unsaturated side chains based on ring size-selective ring-closing metathesis*" Advanced synthesis & Catalyst 2007, vol. 349, 215-230.
Anna Michrowska, et al.: *Nitro-substituted Hoveyda-Grubbs ruthenium carbenes; Enhancement of catalyst activity through electronic activation*. Journal of the American Chemistry Society 2004, vol. 126, 9318-9325.
Georgios C. Vougioukalakis et al.: *Ruthenium-Based Heterocyclic Carbene-Coordinated Olefin Metathesis Catalysts* Chem. Rev. 2010, 110, 1746-1787.
E. Colacino, et al.: "*Preparation of NHC-ruthenium complexes and their catalytic activity in metathesis reaction*" Coordination Chemistry Reviews 251, 2007, 726-764.
W. A. Herrmann.: "*N-Heterocyclische Carbene: en neues Konzept in der metallorganischen Katalyse. Angew*" Chem. 2002, 114, 1342-1363.
C. Slugovc, et al.: "*Thermally switchable olefin metathesis initiators bearing chelating carbenes: influence of the chelate's ring size:*" Organometallics vol. 24. 2005, 2255-2258.

\* cited by examiner

METHOD FOR PREPARATION OF RUTHENIUM-BASED METATHESIS CATALYSTS WITH CHELATING ALKYLIDENE LIGANDS

CROSS REFERENCE TO RELATED APPLICATION

The application is a continuation and claims the benefit of U.S. application Ser. No. 13/318,989, filed on Jan. 5, 2012, which is a 371 of PCT/EP2010/002720 filed on May 4, 2010, and claims priority of EP 09006204.3 filed on May 7, 2009, all which are relied on and incorporated herein by reference.

The present invention relates to a method for the preparation of ruthenium based metathesis catalysts, in particular to the synthesis of ruthenium catalysts, which comprise a chelating alkylidene (carbene) ligand. The method disclosed herein is based on the use of a penta-coordinated Ru-alkylidene complex as starting material for the synthesis via a cross metathesis reaction (CM). The preparation method of the present invention is simple, straightforward, economical and useful for industrial scale.

Olefin metathesis is a fundamental catalytic reaction and one of the most versatile ways to break and create new carbon-carbon bonds and build molecules. Various general metathesis reaction pathways have been described, such as ring-closing metathesis (RCM), ring-opening metathesis polymerization (ROMP), cross metathesis (CM) and their combinations. In the past years, olefin metathesis has become a widely used method for the formation of carbon-carbon bonds in organic synthesis and polymer chemistry.

The development of well-defined molydenum-based carbene catalysts by Schrock and ruthenium-based carbene catalysts by Grubbs has led to a fast growth in the field of metathesis, particularly for industrial applications.

The Grubbs "first generation" catalyst, a ruthenium benzylidene complex bearing two tricyclohexylphosphine ligands, having the structure $(PCy_3)_2Cl_2Ru=CHPh$, was one of the first metathesis catalyst widely used in organic synthesis. This class of catalysts was followed by a more active "second generation" analog, in which N-heterocyclic carbene (NHC) ligands, such as "unsaturated" IMes (=1,3-dimesityl-imidazol-2-ylidene) or "saturated" S-IMes (=$H_2$IMes 1,3-dimesitylimidazolidine-2-ylidene) replaces one phosphine ligand.

Recently, the so-called "boomerang" catalysts are gaining more and more attention. Hoveyda et al. prepared latent metathesis catalysts comprising a benzylidene-ether fragment connected to an alkylidene (carbene) moiety (ref to S. B. Garber, J. S. Kingsbury, B. L. Gray, A. H. Hoveyda, *Amer. Chem. Soc.* 2000, 122, 8168-8179) and WO 02/14376A2. These new type of Ru-catalysts comprise chelating alkylidene ligands (typically alkoxy-benzylidene ligands) and either a $PCy_3$ (first generation) or NHC (second generation) group.

Over the past years, different types of "boomerang catalysts" were disclosed in the literature. Examples from the state of the art are Ru-complexes comprising a cyclic alkoxybenzylidene ligand with an additional ester group (ref to WO 2005/016944A1) or an additional keto group (ref to WO 2008/034552A1). Furthermore, cyclic chelating Ru complexes comprising quinoline and quinoxaline derivates are described in WO 2007/140954. WO 2008/065187A1 discloses cyclic Ru carbene complexes with amido-substituted alkoxybenzylidene ligands, WO 2004/035596 describes a similar complex bearing an alkoxybenzylidene ligand with a nitro-group.

Such "boomerang-type" or "Hoveyda-type" Ru carbene catalysts exhibit a broad application profile in metathesis reactions and may allow for a considerable reduction of the catalyst loading in some applications. Additionally, for some systems recyclability has been described. Therefore, these catalysts are gaining increased importance in commercial applications. Consequently, robust and simple manufacturing pathways for these materials are required, which allow production in Industrial scale.

The general preparation route for chelating "Hoveyda-type" Ru carbene complexes is based on the use of ruthenium carbene complexes of the type $X_2L'L''Ru=CHPh$ (wherein at least one L' or L'' is a phosphine of the type $PR_3$) as precursors. These compounds are reacted with suitable olefinic precursor ligands which comprise an additional donor group. The new carbene bond is generated by cross metathesis reaction ("CM"), while one phosphine ligand (L' or L'') is replaced by the donor group of the olefinic ligand, thus forming a chelating ring complex.

U.S. Pat. No. 7,205,424 teaches the preparation of ruthenium-based olefin metathesis catalysts by a cross metathesis reaction using Ru-indenylidene carbene complexes and an olefin. However, the preparation of Ru-complexes with chelating alkylidene ligands is not disclosed.

S. Blechert et al. (*Synlett* 2001, No 3, 430-432) report the use of a NHC and $PPh_3$-substituted Ru-indenylidene complex as a precursor for the preparation of a chelating Ru-alkoyxbenzylidene catalyst ("Hoveyda-type" catalyst) by ring closing metathesis. However, due to the low yields reported (i.e. about 40%), this method seems not to be economical.

The use of pyridine-substituted ruthenium carbene complexes as precursors for the synthesis of Ru carbene catalysts via cross metathesis (CM) is described in the literature.

A. Hejl, M. W. Day and R. H. Grubbs (*Organometallics* 2006, 25, 6149-6154) describe the preparation of two ruthenium alkylidene complexes comprising an imine donor bonded to the alkylidene moiety. These compounds were prepared starting from a hexa-coordinated ruthenium precursor complex $(H_2$-IMes$)(py)_2Cl_2Ru=CHPh$, comprising two pyridine ligands and a benzylidene group. Yields of 78 to 84% were reported.

The same precursor complex is used for the synthesis of a ruthenium alkylidene complex containing a cyclic butenyl-pyridyl ligand (T. Ung, A. Heyl, R. H. Grubbs and Y. Schrodi, *Organometallics* 2004, 23, 5399-5401).

WO2007/140954 discloses the use of a 3-bromo-pyridine substituted complex $(H_2$-IMes$)(Br$-py$)_2Cl_2Ru=CHPh$ as starting material, again bearing two pyridine-type ligands.

M. Barbasievicz et al, report the synthesis of chelating ruthenium quinoline and quinoxaline complexes starting from the benzylidene compound $(H_2$-IMes$)(PCy_3)Cl_2Ru=CHPh$ and using Cu(I)Cl as phosphine scavenger (ref to *Organometallics* 2006, 25(15), 3599-3604).

Hazardous chemicals, such as diazo reagents (e.g. diazoalkenes) are commonly used in the preparation of ruthenium benzylidene complexes. Therefore, synthesis routes starting from such compounds should be avoided in industrial catalyst production.

It was an objective of the present invention to provide an improved method for preparation of ruthenium-based carbene catalysts with chelating alkylidene ligands ("boomerang-type" catalysts). The new method should provide high yields and should not require the use of hazardous chemicals. Furthermore, the method should provide the ruthenium carbene catalysts in high product purity and without contamination (for example without residues of phosphine ligands or Cu ions). The method should be easily scalable, environmentally friendly and applicable at industrial production scale.

The present invention is directed to these objectives by providing the method according to claim 1 and the subsequent claims dependent thereon.

According to the present invention, ruthenium-based carbene catalysts with a chelating alkylidene ligand are prepared by the reaction of a ruthenium alkylidene starting complex with an olefin derivative via cross metathesis reaction (CM). The method of the present invention employs a penta-coordinated ruthenium (II)-alkylidene catalyst of the type (Py)(L)X$^1$X$^2$ Ru(alkylidene) as starting compound. This starting complex has the general formula

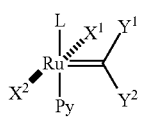

In this formula, L is a neutral ligand, X$^1$ and X$^2$ are, independently from each other, inorganic or organic anionic ligands, such as halide anions, pseudohalide anions, hydroxides, acetates, trifluoracetates or carboxylates and Py stands for an N-heterocyclic two-electron donor ligand. Y$^1$ and Y$^2$ are, independently form each other, hydrogen, C$_1$-C$_6$-alkyl, C$_2$-C$_6$-alkenyl, C$_2$-C$_6$-alkynyl, C$_1$-C$_6$-alkylthio, aryl, arylthio, C$_1$-C$_6$-alkylsulfonyl or C$_1$-C$_6$-alkylsulfinyl. Preferably, Y$^1$ and Y$^2$ are taken together to form a ring of the "Indenylidene" type according to the formula

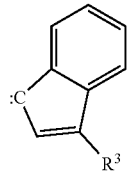

with R$^3$ being hydrogen, a substituted or unsubstituted aryl group or a substituted or unsubstituted phenyl group. In a preferred embodiment, R$^3$ is a substituted or unsubstituted phenyl group. In a further preferred embodiment, the ligand L is a saturated or unsaturated N-heterocyclic carbene ligand ("NHC" ligand) and the Ru(II)-precursor complexes are of the type (Py)(NHC)X$^1$X$^2$Ru(indenylidene) or (Py)(NHC) X$^1$X$^2$Ru(phenyl-indenylidene).

The present invention provides a method for preparing a ruthenium-based carbene catalyst with a chelating alkylidene ligand comprising the reaction of a ruthenium (II)-alkylidene complex with an olefin derivative according to equation (1):

Equation (1):

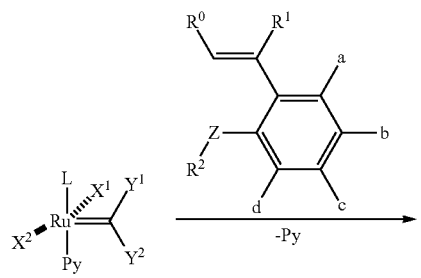

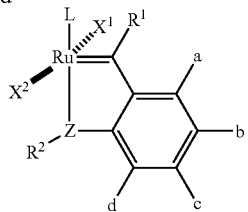

wherein
L is a neutral ligand, preferably a saturated or unsaturated N-heterocyclic carbene ligand ("NHC" ligand), X$^1$ and X$^2$ are, independently from each other, inorganic or organic anionic ligands, such as halide anions, pseudohalide anions, hydroxides, acetates, trifluoracetates or carboxylates, Y$^1$ and Y$^2$ are, independently form each other, hydrogen, C$_1$-C$_6$-alkyl, C$_2$-C$_6$-alkenyl, C$_2$-C$_6$-alkynyl, C$_1$-C$_6$-alkylthio, aryl, arylthio, C$_1$-C$_6$-alkylsulfonyl or C$_1$-C$_6$-alkylsulfinyl, or Y$^1$ and Y$^2$ are taken together to form a ring of the indenylidene type according to the formula

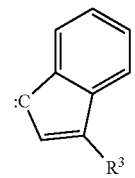

wherein in said formula R$^3$ is hydrogen, a substituted or unsubstituted aryl group or a substituted or unsubstituted phenyl group, Py is an N-heterocyclic two-electron donor ligand, R$^0$ and R$^1$ are, independently from each other, hydrogen, C$_1$-C$_{16}$-alkyl, C$_2$-C$_{10}$-alkenyl, C$_2$-C$_{10}$-alkynyl, a phenyl or an aryl group (which optionally can be substituted), a, b, c and d are, independently from each other, hydrogen, C$_1$-C$_{10}$-alkyl, C$_2$-C$_{10}$-alkenyl, C$_2$-C$_{10}$-alkynyl, a phenyl or aryl group, or an electron withdrawing group ("EWG"), with the provision that each of a, b, c or d can form a ring with each other, Z is a heterodonor atom such as oxygen (O), sulphur (S), nitrogen (N) or a group comprising a heterodonor atom such as sulfinyl (>S=O), R$^2$ is a substituted or unsubstituted hydrocarbon group, such as alkyl, alkenyl, alkynyl, aryl, alkylamino, alkylthio, a substituted or unsubstituted keto group such as —C(R$^a$)$_2$—CO—C(R$^b$)$_3$, a substituted or unsubstituted ester group such as —C(R$^a$)$_2$—CO—O(R$^c$) (wherein in said groups R$^a$ is hydrogen or C$_1$-C$_{10}$-alkyl, R$^b$ is hydrogen, C$_1$-C$_{10}$-alkyl, C$_1$-C$_{10}$-fluoroalkyl, C$_1$-C$_{10}$-alkylamino, C$_1$-C$_{10}$-alkyl ammonium or C$_2$-C$_{10}$-alkenyl and R$^c$ is C$_1$-C$_{10}$-alkyl, C$_1$-C$_{10}$-fluoroalkyl, C$_1$-C$_{10}$-alkylamino, C$_1$-C$_{10}$-alkyl ammonium or C$_2$-C$_{10}$-alkenyl) and wherein R$^2$ and/or Z may form a ring with d.

In a preferred embodiment, the present invention is directed to a method for preparing a ruthenium-based carbene catalyst with a chelating alkylidene ligand comprising the reaction of a ruthenium (II)-alkylidene complex with an olefin derivative according to equation (1), wherein L is a saturated H$_2$IMes (=1,3-dimesityl-imidazolidine-2-ylidene) or unsaturated IMes (=13-dimesityl-imidazole-2-ylidene) ligand, X$^1$ and X$^2$ are, independently from each other, anionic ligands such as Cl—, Br— or I—, Y$^1$ and Y$^2$ are taken together to form a ring of the indenylidene type according to the formula

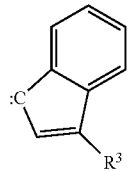

wherein R$^3$ is a substituted or unsubstituted phenyl group,
Py is a substituted or un-substituted pyridine ligand,
R$^0$ and R$^1$ are, independent from each other, hydrogen or a C$_1$-C$_{10}$-alkyl group,
a, b, c and d are, independent from each other, hydrogen, C$_1$-C$_{10}$-alkyl, a phenyl, an aryl group or an electron withdrawing group (EWG) such as F, Cl, Br, I, —CF$_3$, —NO$_2$, —N(H)—CO—CH$_3$, —N(alkyl)-CO—CH$_3$, —N(H)—CO—CF$_3$; —N(alkyl)-CO—CF$_3$, —O$_2$S-(alkyl), —O—CO-(alkyl) or —SO$_2$—N(CH$_3$)$_2$,
Z is a heterodonor atom such as oxygen (O) or nitrogen (N),
R$^2$ is a substituted or unsubstituted alkyl group such as —CH$_3$ or —CH(CH$_3$)$_2$, a substituted or unsubstituted keto group such as —CH$_2$—CO—CH$_3$, —CH$_2$—CO—C$_2$H$_5$, —CH(CH$_3$)—CO—CH$_3$ or —CH(CH$_3$)—CO—C$_2$H$_5$, a substituted or unsubstituted ester group such as —CH$_2$—CO—O—CH$_3$, —CH$_2$—CO—O—C$_2$H$_5$, —CH(CH$_3$)—CO—O—CH$_3$ or —CH(CH$_3$)—CO—O—C$_2$H$_5$ or an amino-group containing ester group such as —CH(CH$_3$)—CO—O—C$_2$H$_4$—N(CH$_3$)$_2$,
and wherein R$^2$ and/or the heterodonor atom Z and d may form a ring.

In a further embodiment of the invention, the substituents of the olefin derivative (specifically R$^2$ or the heterodonor atom Z and substituent d) may form a ring. In this case, the heterodonor atom Z preferably is nitrogen (N) and Z and d form a ring to build up a quinoline ring system, a quinoxaline ring system or an indol ring system.

Generally, Ru(II)-carbene complexes of the type (Py)(L)X$^1$X$^2$Ru(alkylidene) are used as starting compounds in the method of the present invention. Preferably, penta-coordinated ruthenium (indenylidene) carbene complexes are employed. The flu-alkylidene carbene precursors preferably are phosphine free and comprise a "NHC" ligand and a "Py" ligand. Herein, the term "Py" denotes an N-heterocyclic two-electron donor ligand, preferably a substituted or unsubstituted pyridine ligand.

Examples for suitable Py ligands are pyridine, 3-bromo-pyridine or 4-methyl pyridine, quinoline or piperidine. Examples for suitable NHC ligands ("N-heterocyclic carbene" ligands) are saturated H$_2$IMes (=1,3-dimesityl-imidazole-2-ylidene) or unsaturated IMes (=1, 3-dimesityl-imidazole-2-ylidene).

X$^1$ and X$^2$ are, independently from each other, inorganic or organic anionic (i.e. negatively charged) ligands, such as halide anions, pseudohalide anions, hydroxides, acetates, trifluoracetates or carboxylates. Examples for suitable anionic ligands X are the halides Cl—, Br— or I—, with Cl— being most preferred.

R$^3$, which is bonded to the indenylidene moiety, stands for hydrogen, a substituted or unsubstituted aryl or substituted or unsubstituted phenyl group; preferably, R$^3$ is a substituted or unsubstituted phenyl group.

A particularly preferred starting compound is (Py)(H$_2$-IMes)Cl$_2$Ru(3-phenyl-1H-inden-1-ylidene). This complex can be obtained in excellent yields (>90%) in a ligand exchange reaction starting from (H$_2$-IMes)(PCy$_3$)Cl$_2$Ru (phenyl-indenylidene) with excess pyridine (ref to D. Burtscher, C. Lexer, K. Mereiter, R. Winde, R. Karch and C. Slugovc, *J. of Polymer Science: Part A: Polymer Chemistry* 2008, Vol. 46, 4630-4635. Other suitable starting complexes can be prepared by the person skilled in the art by applying similar methods. Due to the generally high yields of these Ru starting compounds, the preparation method of the present invention is straightforward and economical. It can be applied for the preparation of a great variety of ruthenium-based carbene catalysts with chelating alkylidene ligands.

In its preferred versions, the method of the present invention avoids the use of Ru carbene complexes with phosphine ligands L as starting materials. As, in this case, no phosphine ligands L (such as PPh$_3$ or PCy$_3$) are present in the starting complex, less side products (such as free phosphine ligands or phosphine oxides) are produced.

Furthermore, the addition of Cu(I)Cl, frequently used in the prior art as phosphine scavenger in similar cross metathesis processes, is not necessary. This results in high purity products with a very low Cu-content. Typically, the Cu-content of the Ru catalyst products is less than 10 ppm, preferably less than 5 ppm (as determined by ICP; ICP=inductive coupled plasma). As an additional advantage, due to the absence of phosphine ligands in the present method, inert reaction conditions (i.e. a protective gas atmosphere) are not required per se. In many cases, depending on the ligands employed, the preparation method can be performed under regular air atmosphere or at least under non-stringent inert conditions.

Surprisingly, the method of the present invention provides excellent overall yields in the range of 80 to 95%. This may be due to the unique structure of the penta-coordinated Ru (II)-alkylidene complex employed as the starting compound. While the bulky ligand L provides sufficient stability during the reaction, the substitution of the Py ligand by the heterodonor atom (or the heterodonor atom comprising) group Z in the chelating alkylidene moiety occurs rapidly and easily, thus the formation of the chelating ring in the cross metathesis (CM) reaction is facilitated. Consequently, the reaction times are significantly shortened.

The precursors for the chelating alkylidene ligands (hereinafter called "olefin derivative") have the following general formula:

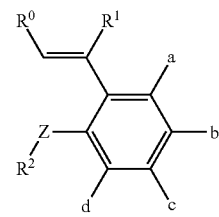

In this formula, $R^0$ and $R^1$ are, independent from each other, hydrogen, $C_1$-$C_{10}$-alkyl, $C_2$-$C_{10}$-alkenyl, $C_2$-$C_{10}$-alkynyl, a phenyl or an aryl group.

The substituents a, b, c and d can be, independent from each other, hydrogen, $C_1$-$C_{10}$-alkyl, $C_2$-$C_{10}$-alkenyl, $C_2$-$C_{10}$-alkynyl, a phenyl or aryl group, or an electron withdrawing group (herein abbreviated "EWG"). Hereinafter, under the term EWG, atoms and/or groups are summarized, which have electron-withdrawing properties and which exhibit higher electronegativity values (EN) compared to hydrogen (H). Examples for suitable EWGs are the halogen atoms F, Cl, Br, I or the groups —$CF_3$, —$NO_2$, —N(H)—CO—$CH_3$, N(alkyl)-CO—$CH_3$, —N(H)—CO—$CF_3$; —N(alkyl)-CO—$CF_3$, —$O_2$S-(alkyl), —O—CO-(alkyl) and —$SO_2$—$N(CH_3)_2$.

Furthermore, each of the substituents a, b, c or d may form a ring with each other.

Z is a heterodonor atom such as oxygen (O), sulphur (S), nitrogen (N) or a group comprising a heterodonor atom, such as sulfinyl (>S=O). Preferably, Z is a heterodonor atom such as oxygen (O) or nitrogen (N).

$R^2$ is a substituted or unsubstituted hydrocarbon group, such as alkyl, alkenyl, alkynyl, aryl, alkylamino, alkylthio, a substituted or unsubstituted keto group such as —$C(R^a)_2$—CO—$C(R^b)_3$, a substituted or unsubstituted ester group such as —$C(R^a)_2$—CO—$O(R^c)$ (herein in said groups $R^a$ is hydrogen or $C_1$-$C_{10}$-alkyl, $R^b$ is hydrogen, $C_1$-$C_{10}$-alkyl, $C_1$-$C_{10}$-alkyl ammonium or $C_2$-$C_{10}$-alkenyl and $R^c$ is $C_1$-$C_{10}$-alkyl, $C_1$-$C_{10}$-alkylamino, $C_1$-$C_{10}$-alkyl ammonium or $C_2$-$C_{10}$-alkenyl) and wherein $R^2$ and/or Z may form a ring with d.

In general, the precursor ligands may be prepared according to standard procedures known from the literature or may be obtained commercially from various suppliers. Examples of olefin derivatives suitable for the method of the present invention are (E/Z)-1-Isopropoxy-2-(1-propenyl)-benzene, (E/Z)-1-[2-(1-propen-1-yl)-phenoxy]-2-propanone), 2-isopropoxy-4-nitro-styrene, 2-isopropoxy-3-vinyl-biphenyl or 8-vinyl-quinolin. The vinyl quinoline and vinyl-quinoxaline derivates are obtainable according to the procedures described in the literature (M. Barbaslevicz et al., ref to above).

Generally, the preparation method of the present invention is conducted in aromatic hydrocarbon solvents or chlorinated hydrocarbon solvents such as dichlormethane or 1,2-dichloroethane. Aromatic hydrocarbon solvents such as benzene, toluene or xylene are preferred. The use of these aromatic hydrocarbon solvents, in particular toluene, provides in most cases the additional advantage that the resulting ruthenium complexes directly precipitate from the reaction mixture thus enabling easy isolation and workup procedures.

The starting Ru(II)-compound (Py)(L)$X^1X^2$Ru(alkylidene) is dissolved in the appropriate solvent and the ligand precursor (olefin derivative) is added. The molar ratio of ligand precursor vs. Ru-starting complex is in the range of 2:1, preferably in the range of 1.1:1. A stoichiometric ratio of both reactants is particularly preferred.

The reaction temperatures are in the range of 0° C. to 150° C., preferably in the range of room temperature (20° C.) to 100° C. The suitable reaction times depend on the type of olefin derivative employed. Typically, the reaction times are in the range from 1 to 8 hours, preferably in the range from 1 to 5 hours and most preferred in the range of 1 to 4 hours.

When using aromatic hydrocarbon solvents (such as benzene, toluene or xylene), in many cases the resulting ruthenium catalyst complexes are sparely soluble and precipitate from the reaction mixture upon cooling and/or solvent reduction. The precipitated products are separated from the reaction mixture by conventional separation techniques (filtration, centrifuging etc), washed with non-polar solvents such as n-hexane or n-heptane and/or polar solvents such as diethylether or ethanol. The products may be dried by conventional drying methods.

Due to the high purity of the resulting products, there is no need for further purification steps (such as chromatography and the like). However, if necessary, additional purification steps such as column chromatography (LC, HPLC etc) may be employed. The preparation method according to the present invention is very versatile and useful for industrial, large scale production of catalysts and can be applied to a great variety of ruthenium-based carbene catalysts with chelating alkylidene ligands.

The Ru-carbene catalysts ("Hoveyda-type catalysts") prepared according to the present invention exhibit a broad application profile in metathesis reactions. The catalyst products can be used in a variety of metathesis reactions, for example in ring-closing metathesis (RCM), ring-opening metathesis polymerization (ROMP), cross metathesis (CM), acyclic diem-metathesis-polymerization (ADMET) and their combinations.

The following examples are intended to describe the invention in more detail, without limiting the scope of protection.

EXAMPLES

General Remarks

The ligand precursors/olefin derivatives employed in the following examples are known compounds, having CAS Registry Nos. They can be prepared according to methods published in the literature and/or procedures known to the person skilled in the art. Details: for (E/Z)-1-Isopropoxy-2-(1-propenyl) benzene: CAS Reg. No. 533934-20-2; for (E/Z)-1-[2-(1-propen-1-yl)-phenoxy]-2-propanone): CAS Reg. No. 1014701-63-3; for 2-isopropoxy-4-nitrostyrene: CAS Reg. No. 753031-08-2; for 8-vinylquinoline: CAS Reg. No. 96911-08-9.

Example 1

Preparation of

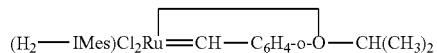

a) Preparation of Starting Compound

The starting complex was prepared according to D. Buitscher et al., *J. of Polymer Science: Part A: Polymer Chemistry* 2008, 46, 4630-4635 starting from ($H_2$-IMes)($PCy_3$)$Cl_2$Ru(phenyl-indenylidene) (metathesis catalyst M2; Umicore AG & Co KG, Hanau) by stirring with excess pyridine (~30 equivalents) under inert atmosphere for 30 minutes at room temperature. Subsequent addition of the reaction mixture to stirred n-heptane and further stirring for 30 minutes at room temperature followed by cooling the reaction mixture overnight (−27° C.) resulted in the formation of a brown precipitate. The precipitate was filtered off, washed with n-heptane and dried in vacuum. The compound is obtained in 95% yield as an orange-brown, microcrystalline solid.

b) Preparation of

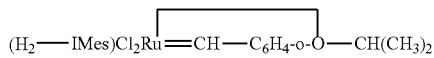

Reaction Equation:

2.5 g catalyst Dichloro-(3-phenyl-1H-Inden-1-ylidene)-(1,3-dimesityl-4,5-dihydro-imidazol-2-ylidene)-(pyridine)-ruthenium(II), [Umicore M31, Umicore AG & Co KG, Hanau] were dissolved in 30 ml of toluene and 0.7 g of (E/Z)-1-Isopropoxy-2-(1-propenyl)benzene dissolved in 10 ml toluene were added. The reaction mixture was stirred for 4 hours at 65° C. and then cooled down to room temperature. The mixture was concentrated under vacuum and a green microcrystalline solid precipitated.

It was filtered and washed with n-hexane and diethyl ether. The green-yellowish product was dried under vacuum (approx. 12 mbar) overnight and characterized by NMR and elemental analysis. Yield: 1.8 g (87%). The analytical data are in agreement with the published data.

Example 2

Preparation of

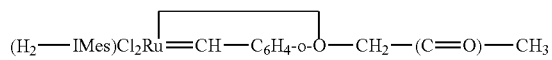

Reaction Equation:

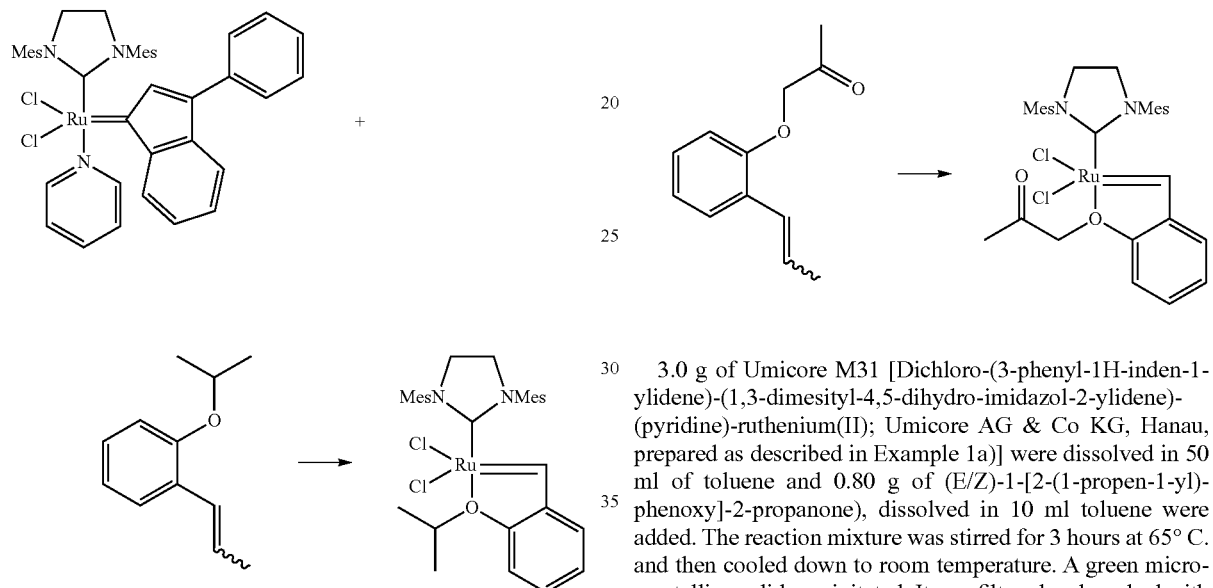

3.0 g of Umicore M31 [Dichloro-(3-phenyl-1H-inden-1-ylidene)-(1,3-dimesityl-4,5-dihydro-imidazol-2-ylidene)-(pyridine)-ruthenium(II); Umicore AG & Co KG, Hanau, prepared as described in Example 1a)] were dissolved in 50 ml of toluene and 0.80 g of (E/Z)-1-[2-(1-propen-1-yl)-phenoxy]-2-propanone), dissolved in 10 ml toluene were added. The reaction mixture was stirred for 3 hours at 65° C. and then cooled down to room temperature. A green microcrystalline solid precipitated. It was filtered and washed with n-hexane and diethyl ether. The green-yellowish product was dried under vacuum overnight and characterized by NMR and elemental analysis. Yield: 2.2 g (87%).

Example 3

Preparation of

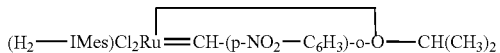

Reaction Equation:

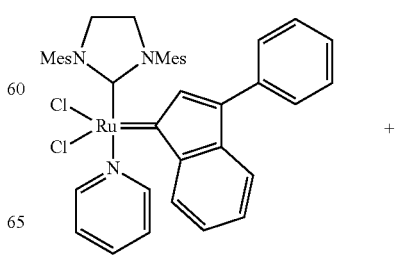

-continued

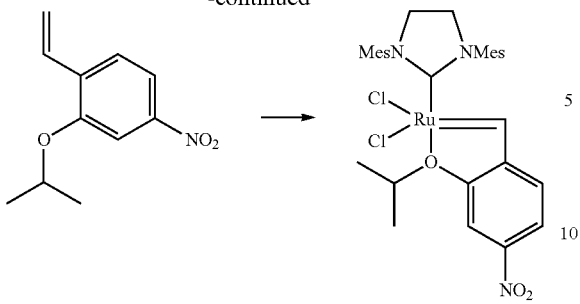

2.5 g catalyst Umicore M31 [Dichloro-(3-phenyl-1H-inden-1-ylidene)-(1,3-dimesityl-4,5-dihydro-imidazol-2-yliden)-(pyridine)-ruthenium(II); Umicore AG & Co KG, Hanau, prepared as described in Example 1a)] were dissolved in 30 ml of toluene and 0.8 g of 2-isopropoxy-4-nitrostyrene dissolved in 10 ml toluene were added. The reaction mixture was stirred for 2 hours at 65° C. and then cooled down to room temperature. The mixture was concentrated under vacuum and a green microcrystalline solid precipitated. It was filtered and washed with n-hexane and diethyl ether. The green-yellowish product was dried under vacuum overnight and characterized by NMR and elemental analysis. Yield: 1.9 g (85%). The analytical data are in agreement with the published data.

Example 4

Preparation of

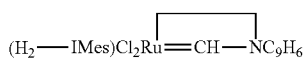

Reaction Equation:

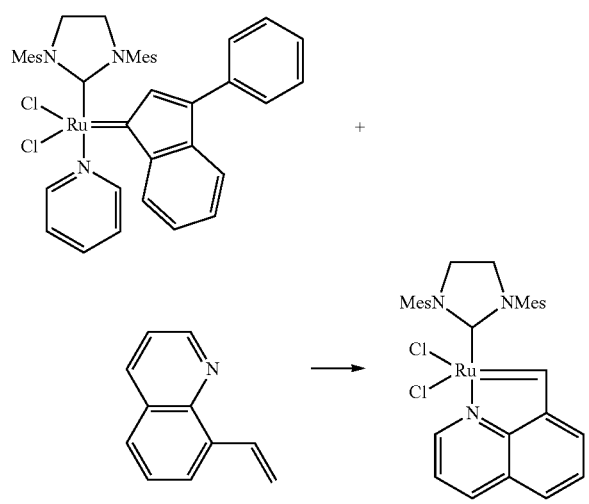

1.0 g catalyst Umicore M31 [Dichloro-(3-phenyl-1H-inden-1-yliden)-(1,3-dimesityl-4,5-dihydro-imidazol-2-yliden)-(pyridine)-ruthenium(II)] (Umicore AG & Co KG, Hanau) were dissolved in 20 ml of toluene and 0.24 g of 8-vinylquinoline dissolved in 5 ml toluene were added. The reaction mixture was stirred for 2 hours at 65° C. and then cooled down to room temperature. The mixture was concentrated under vacuum and a green micro-crystalline solid precipitated. It was filtered and washed with cold n-hexane and diethyl ether. The green-yellowish product was dried under vacuum overnight and characterized by NMR and elemental analysis. Yield: 0.7 g (85%). The analytical data are in agreement with the published data.

Comparative Example (CE1)

Preparation of

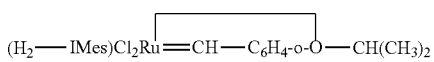

via (H$_2$IMes)(PCy$_3$)Cl$_2$Ru(phenylidenylidene)
Reaction Equation:

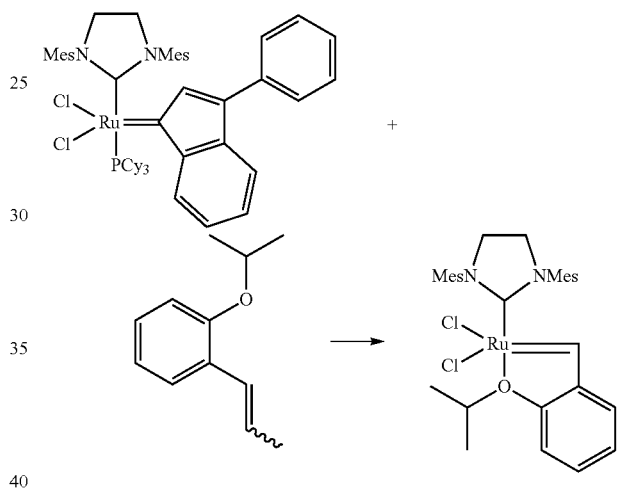

1.15 g (1.2 mmol) of (H$_2$-IMes)(PCy$_3$)Cl$_2$Ru(phenylindenylidene) (Umicore M2, Umicore AG & Co KG, Hanau) was dissolved in 30 ml of toluene and 0.25 g (1.44 mmol, 1.2 eq.) of (E/Z)-1-Isopropoxy-2-(1-propenyl)benzene, dissolved in 10 ml toluene, were added. The reaction mixture was stirred for 6 hours at 65° C. and then cooled down to room temperature. The mixture was concentrated under vacuum to about 15 ml.

Then, 60 ml of pentane were added under stirring. The resulting greenish-brown precipitate was separated by filtration and washed with cold pentane and ethyl acetate. The crude product was suspended in 15 ml toluene, filtered and washed with diethyl ether. The green solid was finally dried overnight under vacuum. A yield of 0.25 g (30%) was obtained.

This yield is significantly lower than the yield obtained by the method according to the invention (ref. to Example 1). Furthermore, due to the presence of a phosphine ligand, additional time-consuming purification steps are necessary and the product purity is reduced.

The invention claimed is:
1. Method for the preparation of a ruthenium-based carbene catalyst with a chelating alkylidene ligand comprising the reaction of a ruthenium (II)-alkylidene complex with an olefin derivative according to the equation:

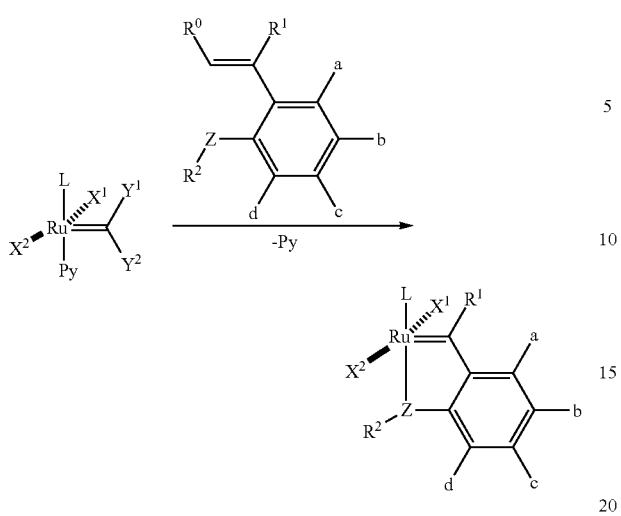

wherein
L is a substituted or unsubstituted imidazole or imidazolidine ring,
$X^1$ and $X^2$ are, independently from each other, inorganic or organic anionic ligands selected from halide anions, pseudohalide anions, hydroxides, acetates, trifluoroacetates or carboxylates,
$Y^1$ and $Y^2$ are, independently from each other, hydrogen, $C_1$-$C_6$-alkyl, $C_2$-$C_6$-alkenyl, $C_2$-$C_6$-alkynyl, $C_1$-$C_6$-alkylthio, aryl, arylthio, $C_1$-$C_6$-alkylsulfonyl or $C_1$-$C_6$-alkylsulfinyl, or $Y^1$ and $Y^2$ are taken together to form a ring of the indenylidene type according to the formula

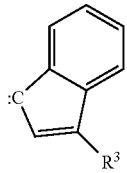

wherein in said formula $R^3$ is hydrogen or a substituted or unsubstituted aryl group,
Py is an N-heterocyclic two-electron donor ligand selected from the group consisting of pyridine, 3-bromo-pyridine, 4-methyl-pyridine, quinolone, and piperidine,
$R^0$ and $R^1$ are, independently from each other, hydrogen, $C_1$-$C_{10}$-alkyl, $C_2$-$C_{10}$-alkenyl, $C_2$-$C_{10}$-alkynyl, or a substituted or unsubstituted aryl group,
a, b, c and d are, independently from each other, hydrogen, $C_1$-$C_{10}$-alkyl, $C_2$-$C_{10}$-alkenyl, $C_2$-$C_{10}$-alkynyl, or aryl group, or an electron withdrawing group ("EWG"), with the provision that two of a, b, c or d can form a ring,
Z is a heterodonor atom selected from the group consisting of oxygen (O), sulphur (S), and nitrogen (N), or a group comprising a heterodonor atom,
$R^2$ is a substituted or unsubstituted hydrocarbon group selected from alkyl, alkenyl, alkynyl, aryl, alkylamino, alkylthio, a hydrocarbon containing a substituted or unsubstituted keto group, a hydrocarbon containing a substituted or unsubstituted ester group and wherein $R^2$ and/or Z may form a quinolone, a quinoxaline, or an indol ring system with d.

2. The method according to claim 1, wherein
L is a saturated $H_2$IMes (=1, 3-dimesityl-imidazolidine-2-ylidene) or unsaturated IMes (=1, 3-dimesityl-imidazole-2-ylidene) ligand,
$X^1$ and $X^2$ are, independently from each other, anionic ligands selected from the group consisting of Cl—, Br—, and I—,
$Y^1$ and $Y^2$ form a ring of the indenylidene type according to the formula

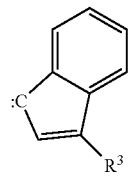

wherein $R^3$ is a substituted or unsubstituted phenyl group,
Py is a substituted or un-substituted pyridine ligand
$R^0$ and $R^1$ are, independently from each other, hydrogen or a $C_1$-$C_{10}$-alkyl group,
a, b, c and d are, independently from each other, hydrogen, $C_1$-$C_{10}$-alkyl, a phenyl, an aryl group or an electron withdrawing group (EWG) selected from the group consisting of F, Cl, Br, I, —$CF_3$, —$NO_2$, —N(H)—CO—$CH_3$, —N(alkyl)-CO—$CH_3$, —N(H)—CO—$CF_3$; —N(alkyl)-CO—$CF_3$, —$O_2$S-(alkyl), —O—CO-(alkyl), and —$SO_2$—N($CH_3$)$_2$,
Z is a heterodonor atom selected from oxygen (O) or nitrogen (N),
$R^2$ is a substituted or unsubstituted alkyl group selected from —$CH_3$ or —CH($CH_3$)$_2$, a substituted or unsubstituted keto group selected from —$CH_2$—CO—$CH_3$, —$CH_2$—CO—$C_2H_5$, —CH($CH_3$)—CO—$CH_3$, or —CH($CH_3$)—CO—$C_2H_5$, a substituted or unsubstituted ester group selected from —$CH_2$—CO—$CH_3$, —$CH_2$—CO—O—$C_2H_5$, —CH($CH_3$)—CO—$CH_3$, or —CH($CH_3$)—CO—O—$C_2H_5$, or —CH($CH_3$)—CO—O—$C_2H_4$—N($CH_3$)$_2$, and
wherein $R^2$ and/or the heterodonor atom Z may form a quinolone, a quinoxaline, or an indol ring system with d.

3. The method according to claim 1, wherein the reaction is a cross metathesis reaction (CM).

4. The method according to claim 1, wherein the reaction is conducted in aromatic hydrocarbon solvents.

5. The method according to claim 1, wherein the reaction temperature is in the range of 20 to 100° C.

6. The method according to claim 1, wherein the molar ratio of olefinic derivative vs. ruthenium (II)-alkylidene complex is in the range of 2:1.

7. The method according to claim 1, wherein the reaction time is in the range of 1 to 8 hours.

8. The method according to claim 1, wherein the olefin derivative is selected from (E/Z)-1-Isopropoxy-2-(1-propenyl)-benzene, (E/Z)-1-[2-(1-propen-1-yl)-phenoxy]-2-propanone), 2-isopropoxy-4-nitro-styrene, 8-vinylquinolin or 2-isopropoxy-3-vinyl-biphenyl.

9. The method according to claim 1, further comprising the separation of the ruthenium-based carbene catalyst with a chelating alkylidene ligand from the reaction mixture by precipitation and filtration.

10. Ruthenium-based carbene catalyst with a chelating alkylidene ligand, obtained by the method according to claim 1, wherein the Cu content is <10 ppm (as determined by ICP), wherein, when Z is nitrogen (N), $R^2$ is an unsubstituted hydrocarbon group selected from alkyl, alkenyl, alkynyl, aryl, alkylamino, alkylthio, a hydrocarbon containing a substituted or unsubstituted keto group, or a hydrocarbon containing a substituted or unsubstituted ester group, and $R^2$ and/or Z may form a quinolone, a quinoxaline, or an indol ring system with d, and wherein, when Z is oxygen (O), $R^2$ is an unsubstituted hydrocarbon group selected from alkenyl, alkynyl, aryl, alkylamino, or alkylthio.

11. The method of claim 1, wherein Z is a group comprising sulfinyl (>S=O).

12. The method of claim 1, wherein $R^2$ is —$C(R^a)_2$—CO—$C(R^b)_3$, wherein in said groups $R^a$ is hydrogen or $C_1$-$C_{10}$-alkyl, and $R^b$ is hydrogen, $C_1$-$C_{10}$-alkyl, $C_1$-$C_{10}$-fluoroalkyl, $C_1$-$C_{10}$-alkylamino, $C_1$-$C_{10}$-alkyl ammonium or $C_2$-$C_{10}$-alkenyl.

13. The method of claim 1, wherein $R^2$ is —$C(R^a)_2$—CO—$O(R^c)$, wherein in said groups $R^a$ is hydrogen or $C_1$-$C_{10}$-alkyl, and $R^c$ is $C_1$-$C_{10}$-alkyl, $C_1$-$C_{10}$-fluoroalkyl, $C_1$-$C_{10}$-alkylamino, $C_1$-$C_{10}$-alkyl ammonium or $C_2$-$C_{10}$-alkenyl.

14. The method of claim 6, wherein the molar ratio of olefinic derivative vs. ruthenium (II)-alkylidene complex is in the range of 1.1:1.

15. The method of claim 7, wherein the reaction time is in the range of 1 to 4 hours.

16. The method of claim 1, wherein the substituted or unsubstituted aryl is phenyl.

* * * * *